United States Patent
Evans et al.

(10) Patent No.: US 10,751,687 B2
(45) Date of Patent: *Aug. 25, 2020

(54) METHOD FOR PREPARING A SORBENT

(71) Applicant: JOHNSON MATTHEY PUBLIC LIMITED COMPANY, London (GB)

(72) Inventors: Matthew James Evans, Cleveland (GB); Paul Thomas Foran, Cleveland (GB); Matthew David Gwydion Lunn, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 193 days.

This patent is subject to a terminal disclaimer.

(21) Appl. No.: 15/578,525

(22) PCT Filed: May 5, 2016

(86) PCT No.: PCT/GB2016/051281
§ 371 (c)(1),
(2) Date: Nov. 30, 2017

(87) PCT Pub. No.: WO2016/193661
PCT Pub. Date: Dec. 8, 2016

(65) Prior Publication Data
US 2018/0169609 A1    Jun. 21, 2018

(30) Foreign Application Priority Data

Jun. 5, 2015    (GB) .................................. 1509824.7

(51) Int. Cl.
| | |
|---|---|
| *B01J 20/02* | (2006.01) |
| *B01J 20/08* | (2006.01) |
| *B01J 20/28* | (2006.01) |
| *B01J 20/30* | (2006.01) |
| *B01J 20/32* | (2006.01) |
| *B01D 15/08* | (2006.01) |
| *B01J 20/12* | (2006.01) |
| *C01B 3/56* | (2006.01) |
| *C07C 7/12* | (2006.01) |
| *C10G 25/00* | (2006.01) |
| *C10L 3/10* | (2006.01) |

(Continued)

(52) U.S. Cl.
CPC .......... *B01J 20/0285* (2013.01); *B01D 15/08* (2013.01); *B01D 53/02* (2013.01); *B01D 53/04* (2013.01); *B01J 20/0237* (2013.01); *B01J 20/08* (2013.01); *B01J 20/12* (2013.01); *B01J 20/2803* (2013.01); *B01J 20/28004* (2013.01); *B01J 20/3028* (2013.01); *B01J 20/3042* (2013.01); *B01J 20/3078* (2013.01); *B01J 20/3085* (2013.01); *B01J 20/3204* (2013.01); *B01J 20/3236* (2013.01); *B01J 20/3293* (2013.01); *C01B 3/56* (2013.01); *C07C 7/12* (2013.01); *C10G 25/003* (2013.01); *C10L 3/101* (2013.01); *B01D 2253/102* (2013.01); *B01D 2253/104* (2013.01); *B01D 2253/106* (2013.01); *B01D 2253/108* (2013.01); *B01D 2253/1124* (2013.01); *B01D 2253/1128* (2013.01); *B01D 2253/25* (2013.01); *B01D 2253/304* (2013.01); *B01D 2253/306* (2013.01); *B01D 2257/60* (2013.01); *B01D 2257/602* (2013.01); *C01B 2203/042* (2013.01)

(58) Field of Classification Search
CPC ........ B01J 20/02; B01J 20/08; B01J 20/0285; B01J 20/0237; B01J 20/0233; B01J 20/28; B01J 20/28002; B01J 20/28004; B01J 20/28011; B01J 20/28016; B01J 20/28019; B01J 20/2803; B01J 20/28057; B01J 20/28061; B01J 20/3007; B01J 20/30; B01J 20/3028; B01J 20/3042; B01J 20/3078; B01D 15/00; B01D 15/08; B01D 53/04; B01D 2253/10; B01D 2253/104; B01D 2253/112; B01D 2253/1122; B01D 2253/1128; B01D 2253/302; B01D 2253/306; B01D 2257/60; B01D 2257/602; C07C 7/12; C10G 25/003
See application file for complete search history.

(56) References Cited

U.S. PATENT DOCUMENTS

| | | |
|---|---|---|
| 2,915,365 A | 12/1959 | Saussol |
| 3,226,191 A | 12/1965 | Osment et al. |

(Continued)

FOREIGN PATENT DOCUMENTS

| | | |
|---|---|---|
| CN | 102046269 A | 5/2011 |
| CN | 104105536 A | 10/2014 |

(Continued)

OTHER PUBLICATIONS

GB1509824.7, Search Report Under Section 17(5) dated Dec. 14, 2015.
GB1607837,0, Combined Search and Examination Report under Sections 17 and 18(3) dated Dec. 21, 2016.
PCT/GB2016/051281, Written Opinion dated Aug. 5, 2016.
PCT/GB2016/051281, International Search Report dated Aug. 5, 2016.
PCT/GB2016/051279, Written Opinion dated Jul. 18, 2016.
PCT/GB2016/051280, Written Opinion dated Aug. 5, 2016.

(Continued)

*Primary Examiner* — Katherine Zalasky McDonald
(74) *Attorney, Agent, or Firm* — BakerHostetler

(57) ABSTRACT

A method is described for preparing a sorbent precursor comprising the steps of: (i) forming agglomerates comprising a particulate support material, (ii) coating the agglomerates with a coating mixture powder comprising a particulate sulphidable copper compound and a particulate calcined, rehydratable alumina to form a coated agglomerate, and (iii) drying the coated agglomerate to form a dried sorbent precursor. The sorbent precursor may be sulphided and used to remove heavy metals such as mercury from fluid streams.

24 Claims, No Drawings

(51) Int. Cl.
*B01D 53/02* (2006.01)
*B01D 53/04* (2006.01)

(56) References Cited

U.S. PATENT DOCUMENTS

| | | | | |
|---|---|---|---|---|
| 4,094,777 A * | 6/1978 | Sugier | ............... | B01D 15/00 210/670 |
| 4,902,662 A * | 2/1990 | Toulhoat | ............... | B01D 53/64 502/216 |
| 4,909,926 A * | 3/1990 | Yan | ............... | C10G 25/00 208/251 R |
| 5,024,683 A * | 6/1991 | Tooley | ............... | B01D 53/02 95/141 |
| 5,120,515 A * | 6/1992 | Audeh | ............... | B01D 53/02 423/210 |
| 5,190,908 A * | 3/1993 | Audeh | ............... | B01D 53/02 423/210 |
| 5,223,145 A * | 6/1993 | Markovs | ............... | B01D 15/00 210/673 |
| 5,245,106 A * | 9/1993 | Cameron | ............... | B01D 53/64 423/215.5 |
| 5,401,393 A * | 3/1995 | Whitehurst | ............... | C10G 25/02 208/251 R |
| 5,948,726 A * | 9/1999 | Moskovitz | ............... | B01D 53/02 423/604 |
| 5,955,393 A * | 9/1999 | Moskovitz | ............... | B01D 53/02 204/157.44 |
| 5,985,790 A * | 11/1999 | Moskovitz | ............... | B01J 20/06 423/604 |
| 2001/0009884 A1* | 7/2001 | Moskovitz | ............... | B01D 53/02 502/263 |
| 2007/0037991 A1 | 2/2007 | Rizkalla et al. | | |
| 2007/0122327 A1* | 5/2007 | Yang | ............... | B01D 53/02 423/210 |
| 2009/0155148 A1* | 6/2009 | Kanazirev | ............... | C10G 25/003 423/210 |
| 2009/0297885 A1 | 12/2009 | Gadkaree et al. | | |
| 2010/0320153 A1 | 12/2010 | Cousins et al. | | |
| 2013/0053234 A1* | 2/2013 | Fish | ............... | B01D 53/64 502/10 |
| 2013/0202503 A1* | 8/2013 | Simonetti | ............... | C10L 3/101 423/210 |
| 2014/0155260 A1* | 6/2014 | Turbeville | ............... | B01J 20/20 502/407 |

FOREIGN PATENT DOCUMENTS

| | | |
|---|---|---|
| GB | 1042158 A1 | 9/1966 |
| WO | WO2009101429 A1 | 8/2009 |
| WO | 2009145877 A1 | 12/2009 |
| WO | 2010061212 A1 | 6/2010 |
| WO | WO2011021024 A1 | 2/2011 |
| WO | 2011081836 A2 | 7/2011 |
| WO | 2013119357 A1 | 8/2013 |
| WO | 2014016560 A1 | 1/2014 |
| WO | 2014016561 A1 | 1/2014 |
| WO | 2015015068 A1 | 2/2015 |
| WO | WO2015092358 A1 | 6/2015 |
| WO | WO2015092359 A1 | 6/2015 |

OTHER PUBLICATIONS

T. Ohtani, et al., "Synthesis of Binary Copper Chalcogenides by Mechanical Alloying," Materials Research Bulletin, vol. 30, No. 12, pp. 1495-1504, 1995.

* cited by examiner

METHOD FOR PREPARING A SORBENT

CROSS-REFERENCE TO RELATED APPLICATIONS

This application is the National Stage of International Patent Application No. PCT/GB2016/051281 filed May 5, 2016, which claims priority from Great Britain Patent Application No. 1509824.7 filed Jun. 5, 2015, the disclosures of each of which are incorporated herein by reference in their entirety.

This invention relates to a method for preparing a sorbent, in particular a method for preparing sorbents comprising copper.

Copper sulphide containing sorbents may be used to remove heavy metals from fluid streams. Heavy metals such as mercury are found in small quantities in fluid streams such as hydrocarbon or other gas and liquid streams. Arsenic and antimony may also be found in small quantities in hydrocarbon streams. Mercury, in addition to its toxicity, can cause failure of aluminium heat exchangers and other processing equipment. Therefore there is a need to efficiently remove these metals from fluid streams, preferably as early as possible in the process flowsheet.

Copper sorbents are conventionally pelleted compositions or granules formed from precipitated compositions containing copper.

WO2009/101429 discloses a method for making an absorbent comprising the steps of: (i) forming a composition comprising a particulate copper compound capable of forming copper sulphide, a particulate support material, and one or more binders, (ii) shaping the composition to form an absorbent precursor, (iii) drying the absorbent precursor material, and (iv) sulphiding the precursor to form the absorbent. The sulphiding agent used to sulphide the absorbent precursor may be one or more sulphur compounds such as hydrogen sulphide, carbonyl sulphide, mercaptans and polysulphides, or mixtures of these. Hydrogen sulphide is preferred.

WO2011/021024 discloses a method for making a sorbent comprising the steps of: (i) applying, from a solution or a slurry, a layer of a copper compound on the surface of a support material, and (ii) drying the coated support material, wherein the thickness of the copper compound layer on the dried support is in the range 1-200 µm. In the Examples, the layer of copper compound was formed from a solution of copper ammine carbonate or from a slurry of basic copper carbonate. The precursor was converted to a sorbent suitable for removing heavy metals from liquids or gases by applying one or more sulphur compounds to sulphide the copper compound and form CuS.

Whereas this method provides coated copper sorbents, there is a need to improve physical properties of the sorbents, such as attrition, for more challenging duties.

Accordingly the invention provides a method for preparing a sorbent precursor comprising the steps of:
(i) forming agglomerates comprising a particulate support material,
(ii) coating the agglomerates with a coating mixture powder comprising a particulate sulphidable copper compound and a particulate calcined, rehydratable alumina to form a coated agglomerate, and
(iii) drying the coated agglomerate to form a dried sorbent precursor.

The invention further provides a method for preparing a sorbent comprising the step of sulphiding the sorbent precursor with one or more sulphur compounds.

The invention further provides a sorbent obtainable by the method and the use of the sorbent in removing heavy metals such as mercury, arsenic selenium, cadmium and antimony from heavy metal-containing fluid streams.

By "sorbent" we include absorbent and adsorbent.

By "calcined, rehydratable alumina" we mean a calcined amorphous or poorly crystalline transition alumina comprising one or more of rho-, chi- and pseudo gamma-aluminas. Such aluminas are capable of rehydration and can retain substantial amounts of water in a reactive form. Calcined, rehydratable aluminas are commercially available, for example as "CP alumina powders" available from BASF AG. They may be prepared, for example, by milling gibbsite $(Al(OH)_3)$, to a 1-20 micron particle size followed by flash calcination for a short contact time as described in U.S. Pat. No. 2,915,365. In addition to gibbsite, amorphous aluminium hydroxide and other naturally found mineral crystalline hydroxides such as Bayerite and Nordstrandite or monoxide hydroxides, such as Boehmite (AlOOH) and Diaspore may be also used as a source of the calcined, rehydratable alumina.

The agglomerates may be described as inert "cores" on which the coating mixture powder comprising the sulphidable copper compound and calcined rehydratable alumina are coated. Because the cores are inert, copper compounds are not included. The agglomerates comprise a particulate support material and optionally one or more binders. Such support materials include alumina, metal-aluminate, silica, titania, zirconia, zinc oxide, aluminosilicates, zeolites, metal carbonate, silicon carbide, carbon, or a mixture thereof. The support material offers a means to adapt the physical properties of the sorbent to the duty. Thus the surface area, porosity and crush strength of the sorbent may suitably be tailored to its use. Support materials are desirably oxide materials, such as aluminas, titanias, zirconias, silicas and aluminosilicates, or mixtures of two or more of these. Hydrated oxides may also be used, for example alumina trihydrate or boehmite.

The particulate support material is desirably in the form of a powder, more preferably a powder with a $D_{50}$ particle size in the range 1-100 µm, preferably 1-20 µm, especially 1-10 µm.

A particularly suitable support material is a particulate calcined, rehydratable alumina. The particulate calcined, rehydratable alumina is preferably a calcined amorphous or poorly crystalline transition alumina comprising one or more of rho-alumina, chi-alumina and pseudo-gamma alumina. Preferably the particulate calcined, rehydratable alumina consists of one or more of rho-alumina, chi-alumina and pseudo-gamma alumina, especially rho-alumina. The particulate calcined, rehydratable alumina is desirably in the form of a powder, more preferably a powder with a $D_{50}$ particle size in the range 1-100 µm, preferably 1-20 µm, especially 1-10 µm. The BET Surface area of the calcined, rehydratable alumina as determined by nitrogen adsorption may be in the range 200-400 $m^2/g$, preferably 250-300 $m^2/g$.

Binders that may be used to prepare the agglomerates include clay binders such as bentonite, sepiolite, minugel and attapulgite clays; cement binders, particularly calcium aluminate cements such as ciment fondu; and organic polymer binders such as cellulose binders, or a mixture thereof. Particularly strong agglomerates may be formed where the binder is a combination of a cement binder and a clay binder. In such materials, the relative weights of the cement and clay binders may be in the range 1:1 to 3:1 (first to second binder). The total amount of the binder in the agglomerate may be in the range 5-30% by weight. The one or more binders are desirably in the form of powders, more preferably powder with a $D_{50}$ particle size in the range 1-100 μm, especially 1-20 μm.

However, we have found that where a particulate calcined, rehydratable alumina is used to prepare the agglomerates, they do not require the inclusion of a binder. Thus in a preferred embodiment, the agglomerates are formed simply by granulating, in the absence of other materials, a particulate calcined, rehydratable alumina consisting of an calcined amorphous alumina or a transition alumina comprising one or more of rho-alumina, chi-alumina and pseudo-gamma alumina, especially rho-alumina.

The support material is granulated in a granulator to form agglomerates, which provide a core essentially free of copper compounds. The agglomerates may be formed by mixing a powder composition with a little liquid, such as water, insufficient to form a slurry, and then causing the composition to agglomerate into roughly spherical granules in a granulator. The amount of liquid added will vary depending upon the porosity and wettability of the components, but may be 0.1 to 0.6 ml/g of support material. Aqueous or non-aqueous liquids may be used, but water is preferred. Granulator equipment is available commercially. The agglomerates preferably have a diameter in the range 1-15 mm.

The agglomerates may be aged and/or dried before coating to enhance their strength. Ageing and/or drying is preferably performed at 20-90° C. for 0.5-24 hours. Where calcined, rehydratable alumina is used as the support material the ageing temperature is preferably 40-90° C. An advantage of using just the calcined, rehydratable alumina to prepare the agglomerates is that the ageing step may be considerably reduced or eliminated. Thus ageing may be performed on alumina agglomerates prepared using a calcined, rehydratable alumina at 20-90° C., preferably 40-90° C. for a period of 0.5-8 hours, preferably 0.5-6 hours, more preferably 0.5-2 hours.

In a preferred embodiment, the agglomerates consist of the granulated particulate calcined, rehydratable alumina. Such agglomerates provide a high strength core on which to place the particulate sulphidable copper compound.

The particulate sulphidable copper compound suitable for use in the sorbent precursor is one that may be readily sulphided such as copper oxide and/or basic copper carbonate. One or more sulphidable copper compounds may be present. A preferred particulate copper compound comprises basic copper carbonate, which is a copper hydroxycarbonate. The particulate copper compound may be commercially sourced or may be generated, e.g. by precipitation from a solution of metal salts using alkaline precipitants. Thus the particulate copper compound may be made by precipitating copper-hydroxycarbonate and optionally zinc-hydroxycarbonate using an alkali metal carbonate and/or alkali metal hydroxide precipitant mixture, followed by washing and drying the precipitate. Thus the particulate copper compound may include one or more of azurite $Cu_3(CO_3)_2(OH)_2$; malachite $Cu_2CO_3(OH)_2$; zincian malachite $Cu_{2-x}Zn_xCO_3(OH)_2$; rosasite $Cu_{2-x}Zn_xCO_3(OH)_2$, aurichalcite $Cu_{5-x}Zn_x(CO_3)_2(OH)_6$ and alumina-containing copper-zinc hydroxycarbonate hydrotalcite-type materials where alumina is included during the precipitation, e.g. $Cu_xZn_{6-x}Al_2(OH)_{16}CO_3.4H_2O$. The particulate copper compound is desirably in the form of a powder, more a preferably a powder with an average particle size, i.e. $D_{50}$, in the range 5-100 μm.

Unlike the granulated or extruded products, the copper content of the sorbent precursor is relatively low and may be in the range 0.5-35% by weight, preferably 0.5-30% by weight, most preferably 5-20% by weight, (expressed as copper present in the dried sorbent precursor). Although this level may be less than the amount in conventional granulated materials, the effectiveness of the coated sorbents has surprisingly been found to match these products in terms of mercury captured.

The coating mixture comprises a particulate sulphidable copper compound and a particulate calcined, rehydratable alumina. Preferably the particulate calcined, rehydratable alumina consists of a calcined amorphous alumina or a transition alumina comprising one or more of rho-alumina, chi-alumina and pseudo-gamma alumina, especially rho-alumina. The amount of particulate copper compound in the coating mixture may be in the range 50-95% by weight, preferably 50-90% by weight, more preferably 55-75% by weight, most preferably 60-70% by weight.

The particulate calcined, rehydratable alumina in the coating mixture may be the same or different to a particulate calcined, rehydratable alumina used in the agglomerates but preferably is the same.

A binder may be included in the coating mixture, but this is not necessary.

Other components are not necessary and so the coating mixture preferably consists of a particulate sulphidable copper compound and a particulate calcined rehydratable alumina comprising a calcined amorphous alumina or a transition alumina comprising one or more of rho-alumina, chi-alumina and pseudo-gamma alumina, especially rho-alumina. Because of the calcined rehydratable alumina, binders are not required in the coating mixture.

The coating mixture may be prepared by simply mixing the particulate sulphidable copper compound and the particulate calcined rehydratable alumina, using conventional blending techniques.

The coating mixture is combined with the agglomerates to form coated agglomerates that have a layer of particulate sulphidable copper compound on their surface. This may be achieved conveniently by simply adding the coating mixture to the agglomerates as they are tumbled in the granulator. Other coating techniques may be used. The coated agglomerates may be formed with or without adding additional liquid. Minimizing the amount of liquid used advantageously reduces their drying time and reduces the possibility of forming agglomerates of the coating mixture itself which is undesirable. Additional liquid may however be required. The amount of liquid used may be 0.1 to 0.6 ml/g of coating mixture. Aqueous or non-aqueous liquids may be used, but water is preferred. The water may be mains water, demineralised water, deionised water and the like and is preferably low in dissolved mineral content. The liquid, if required, may conveniently be added by spraying.

The size of the coated agglomerates is largely determined by the size of the original agglomerates. Thus the coated agglomerates preferably have a diameter in the range 1-15 mm.

The copper compound is present in a layer on the surface of the agglomerate. The thickness of the layer in the dried sorbent precursor may be in the range 1 to 2000 μm (micrometres), but preferably is in the range 1-1500 micrometres, more preferably 1-500 micrometres. Thinner layers make more efficient use of the applied copper.

A particularly preferred sorbent precursor comprises a mixture of a particulate basic copper carbonate and a particulate calcined, rehydratable alumina, coated as a surface layer of 1 to 2000 μm thickness on the surface of 1-15 mm agglomerates formed from a particulate calcined, rehydratable alumina support material. Accordingly the sorbent may be formed in the absence of a cement binder or a clay binder.

The coated agglomerates may be aged to enhance their strength before drying. Ageing of the calcined, rehydratable alumina-containing sorbents may be performed at 20-90° C., preferably 40-90° C. An advantage of using just the calcined, rehydratable alumina in the sorbent is that the ageing step may be considerably reduced or eliminated compared to prior art materials. Thus ageing may be performed on the coated agglomerates for 0.5-8 hours, preferably 0.5-6 hours, more preferably 0.5-2 hours before drying.

The coated agglomerates are dried. The drying temperature is preferably kept ≤200° C., more preferably ≤150° C. to avoid bulk decomposition of the sulphidable copper compounds. Drying temperatures up to 120° C. are more preferred, for example the coated agglomerate may conveniently be dried at about 70-120° C. in air. Drying times may be in the range 0.25-16 hours.

The dried sorbent precursor may be sieved to give a desired size fraction.

The dried sorbent precursor may be sulphided to convert the copper compound to copper sulphide and the resulting copper sulphide-coated sorbent used to remove heavy metals from fluid streams. By the term "heavy metal" we include mercury, arsenic, lead, cadmium and antimony, but the sorbent of the present invention is particularly useful for removing mercury and arsenic, especially mercury from fluid streams.

Whereas the dried sorbent precursor may be calcined, e.g. by heating it to a temperature in the range 250-500° C. in air or inert gas, to convert the copper compounds to copper oxide, this is not necessary, as we have found that the copper compounds may be directly sulphided without this additional step.

The sulphiding step, which converts the copper compounds to copper (II) sulphide, CuS, may be performed by reacting the sulphidable copper compound in the layer with a sulphur compound selected from hydrogen sulphide, alkali metal sulphide, ammonium sulphide, or a polysulphide. Hydrogen sulphide is preferred and may conveniently be used as a gas mixture with an inert gas. The gas mixture may, if desired, contain other sulphur compounds such as carbonyl sulphide or volatile mercaptans. The inert gases may be nitrogen, helium or argon; nitrogen is preferred. Carbon dioxide may also be used. The sulphiding gas mixture is preferably free of reducing gases such as hydrogen and carbon monoxide, but these may be present where the sulphiding step is performed at temperatures below 150° C., particularly below 100° C. Hydrogen sulphide is preferably provided to the dried sorbent precursor in gas streams at concentrations of 0.1 to 5% by volume. Sulphiding temperature is preferably ≤150° C., e.g. in the range 1 to 150° C., more preferably ≤120° C., e.g. 1 to 100° C.

The sulphiding step may be performed on the dried sorbent precursor ex-situ in a sulphiding vessel through which a sulphiding agent is passed, or the sulphiding step may be performed in situ, in which case the dried sorbent precursor composition is installed and undergoes sulphidation in the vessel in which it is used to absorb heavy metals. In-situ sulphiding may be achieved using a sulphiding agent stream or where the stream containing heavy metal also contains sulphur compounds, the heavy metal-containing stream itself. Where such concomitant sulphiding and heavy metal absorption occurs, the amount of sulphur compound that is present depends on the type of sulphur compound and metal compound used. Usually, a concentration ratio, as defined by the ratio of sulphur compound (expressed as hydrogen sulphide) concentration (v/v) to heavy metal concentration (v/v), of at least one, and preferably of at least 10 is used so that the precursor is sufficiently sulphided. Should the initial concentration of the sulphur compound in the feed stream be below the level necessary to establish the desired ratio of sulphur compound to heavy metal concentration then it is preferred that the concentration of the sulphur compound is increased by any suitable method. The sulphided sorbent prepared according to the present invention is preferably pre-sulphided, in particular where the fluid to be treated contains free water.

Preferably ≥80% wt of the copper present in the sorbent precursor is sulphided, more preferably ≥90% wt, more preferably ≥95% wt. Essentially all of the sulphided copper in the sorbent is desirably in the form of copper (II) sulphide, CuS.

The sorbent may be used to treat both liquid and gaseous fluid streams containing heavy metals, in particular fluid streams containing mercury and/or arsenic. In one embodiment, the fluid stream is a hydrocarbon stream. The hydrocarbon stream may be a refinery hydrocarbon stream such as naphtha (e.g. containing hydrocarbons having 5 or more carbon atoms and a final atmospheric pressure boiling point of up to 204° C.), middle distillate or atmospheric gas oil (e.g. having an atmospheric pressure boiling point range of 177° C. to 343° C.), vacuum gas oil (e.g. atmospheric pressure boiling point range 343° C. to 566° C.), or residuum (atmospheric pressure boiling point above 566° C.), or a hydrocarbon stream produced from such a feedstock by e.g. catalytic reforming. Refinery hydrocarbon steams also include carrier streams such as "cycle oil" as used in FCC processes and hydrocarbons used in solvent extraction. The hydrocarbon stream may also be a crude oil stream, particularly when the crude oil is relatively light, or a synthetic crude stream as produced from tar oil or coal extraction for example. Gaseous hydrocarbons may be treated using the process of the invention, e.g. natural gas or refined paraffins or olefins, for example. Off-shore crude oil and off-shore natural gas streams in particular may be treated with the sorbent. Contaminated fuels such as petrol or diesel may also be treated. Alternatively, the hydrocarbon may be a condensate such as natural gas liquid (NGL) or liquefied petroleum gas (LPG), or gases such as a coal bed methane, landfill gas or biogas. Gaseous hydrocarbons, such as natural gas and associated gas are preferred.

Non-hydrocarbon fluid streams which may be treated using the sorbent include carbon dioxide, which may be used in enhanced oil recovery processes or in carbon capture and storage, solvents for decaffeination of coffee, flavour and fragrance extraction, solvent extraction of coal etc. Fluid streams, such as alcohols (including glycols) and ethers used in wash processes or drying processes (e.g. triethylene glycol, monoethylene glycol, Rectisol™, Purisol™ and methanol), may be treated by the inventive process. Mercury may also be removed from amine streams used in acid gas removal units. Natural oils and fats such as vegetable and fish oils may be treated, optionally after further processing such as hydrogenation or transesterification e.g. to form biodiesel.

Other fluid streams that may be treated include the regeneration gases from dehydration units, such as molecular sieve off-gases, or gases from the regeneration of glycol driers.

The sorbent is of utility where the fluid stream contains water, preferably in low levels in the range 0.02 to 1% vol. Higher levels up to 5% vol may be tolerated for short periods. The sorbents may be regenerated simply after prolonged exposure to water simply by purging with a dry gas, preferably a dry inert gas such as nitrogen.

Preferably the sorption of heavy metal is conducted at a temperature below 150° C., preferably at or below 120° C. in that at such temperatures the overall capacity for heavy metal sorption is increased. Temperatures as low as 4° C. may be used. A preferred temperature range is 10 to 80° C. The gas hourly space velocity through the sorbent may be in the range normally employed.

Furthermore, the present invention may be used to treat both liquid and gaseous fluid streams containing one or more reductants such as hydrogen and/or carbon monoxide, notably hydrogen. In one embodiment, the fluid stream is a liquid hydrocarbon stream containing dissolved hydrogen and/or carbon monoxide. In another embodiment, the fluid stream is a gaseous stream containing hydrogen and/or carbon monoxide, i.e. a reducing gas stream. Gas streams that may benefit from this process include synthesis gas streams from conventional steam reforming processes and/or partial oxidation processes, and synthesis gas streams from a coal gasifier, e.g. as part of a IGCC process, after gas washing and heat recovery (cooling) steps, and before the sour shift stage. Other streams that may benefit from the present invention include refinery vent streams, refinery cracker streams, blast furnace gases, reducing gases, particularly hydrogen-rich gas streams, ethylene-rich streams and liquid or gaseous hydrocarbon streams, e.g. naphtha, fed or recovered from hydrotreating processes, such as hydrodesulphurisation or hydrodenitrification.

In use, the sorbent may be placed in a sorption vessel and the fluid stream containing a heavy metal is passed through it. Desirably, the sorbent is placed in the vessel as one or more fixed beds according to known methods. More than one bed may be employed and the beds may be the same or different in composition.

The invention is further described by reference to the following Examples.

EXAMPLE 1

Agglomerates were formed by tumbling a calcined, rehydratable alumina powder in a rotating pan and adding water sprayed via a fine mist onto the alumina. The water content of the freshly granulated agglomerates before drying was found to be 29.7 wt %. Following granulation, the material was aged at 45° C. for 1 hour.

The properties of the calcined, rehydratable alumina powder were as follows:

|  | (wt %) |
| --- | --- |
| Chemical composition | |
| Residual Moisture (dried a 250° C. for 30 minutes) | 2 |
| Total loss on ignition (250-1100° C.) | 7 |
| $SiO_2$ | <0.02 |
| $Fe_2O_3$ | <0.01 |
| $Na_2O$ | <0.4 |
| Physical Properties | |
| Surface area | 270 m²/g |
| Packed bulk density | 38 lb/ft³ |
| Particle size distribution (average size) | 5 μm |
| Particle size distribution (90 wt % <) | 12 μm |
| XRD Phase | Amorphous |

A coating mixture consisting of basic copper carbonate and the same calcined, rehydratable alumina was then applied to the alumina agglomerates. The recipe for the coating mixture was as follows:

| Component | % |
| --- | --- |
| Basic copper carbonate (100%), Adchem | 67 |
| Calcined, rehydratable alumina CP-5, BASF | 33 |

The amount of coating mixture was adjusted to produce a copper loading in the finished dried product of 18% wt (expressed as Cu). A coating layer (thickness about 1000 μm) was formed by was formed by adding the coating mixture to the alumina agglomerates in a rotating pan with further addition of water. Following coating, the material was aged at 65° C. before being dried in a fluid bed dryer at 105° C. The dried sorbent precursor product was sieved to provide the sorbent in two size ranges, 1.00-2.80 mm and 2.80-4.75 mm.

The physical properties of the sorbent precursor were determined, and are shown below compared to a sorbent precursor comprising basic copper carbonate, cement and clay binders, and an alumina trihydrate (ATH) support material, prepared according to the method described in WO2009/101429.

The tapped bulk density (TBD) was measured by pouring approximately 500 mls of sorbent granules into a 500 ml plastic measuring cylinder and tapping it until a constant volume was achieved. The TBD was calculated by dividing the mass of sorbent by the tapped volume.

The drum tumbling loss (DrTL) was measured by rotating 100 g of sorbent through 1800 total revolutions at 60 rpm for 30 minutes according to the ASTM method D4058-96. The DrTL is reported as a percentage of the original mass.

The mean crush strength (MCS) was determined by crushing 25 granules of each sorbent using an Engineering Systems C53 machine to calculate mean crush strength based on a normal distribution.

| Example | Description | Ageing time (h) | TBD (g cm$^{-3}$) | DrTL (%) | MCS (kgF) |
| --- | --- | --- | --- | --- | --- |
| 1(a) | Coated sorbent precursor 1.00-2.80 mm | 4 | 0.99 | 0.00 | 8.06 |
| 1(b) | Coated sorbent precursor 2.80-4.75 mm | 4 | 0.99 | 0.00 | 10.38 |
| Comparative | WO2009/101429 2.80-4 mm | 4 | 1.03 | 2.8 | 2.7 |

The use of a calcined, rehydratable alumina provided a much stronger product when compared to the prior art material produced using mixed binders and aluminium trihydrate. The rate at which strength develops also occurs much more rapidly in the calcined rehydratable alumina product when compared to the mixed binder product with strength achieved almost 4 times higher for the same ageing time.

The invention claimed is:

1. A method for preparing a dried sorbent precursor comprising the steps of:
    (i) forming agglomerates comprising a particulate support material in a granulator with a liquid, and ageing the agglomerates to form aged agglomerates of the particulate support material,
    (ii) adding a coating mixture powder to the aged agglomerates, wherein the coating mixture powder comprises a particulate sulphidable copper compound and a particulate calcined, rehydratable alumina, to form coated agglomerates comprising the aged agglomerates having surface layers of the coating mixture powder, and (iii) drying the coated agglomerates to form the dried sorbent precursor.

2. A method according to claim 1 wherein the support material is alumina, metal-aluminate, silicon carbide, silica, titania, zirconia, zinc oxide, aluminosilicate, zeolite, metal carbonate, carbon, or a mixture thereof.

3. A method according to claim 1, wherein the support material is a particulate calcined, rehydratable alumina.

4. A method according to claim 1, wherein the calcined rehydratable alumina comprises a calcined amorphous alumina or a transition alumina that is one or more of rho-alumina, chi-alumina, or pseudo gamma-alumina.

5. A method according to claim 1, wherein the support material is a powder with a $D_{50}$ particle size in a range of from 1 μm to 100 μm.

6. A method according to claim 1, wherein a binder that is a clay binder, cement binder, or organic polymer binder is combined with the support material to form the agglomerates.

7. A method according to claim 6 wherein the binder combined with the support material is a combination of a cement binder and a clay binder.

8. A method according to claim 1, wherein the coated agglomerates have a diameter in a range of from 1 mm to 15 mm.

9. A method according to claim 1, wherein the particulate sulphidable copper compound is one or more compounds that is copper oxide, basic copper carbonate, or a precipitated material comprising copper basic carbonate and zinc basic carbonate.

10. A method according to claim 1, wherein the particulate sulphidable copper compound is a powder with an average particle size, $[D_{50}]$, in a range of from 5 μm to 100 μm.

11. A method according to claim 1, wherein a copper content of the dried sorbent precursor is in a range of 0.5 to 35% by weight expressed as copper present in the dried sorbent precursor.

12. A method according to claim 1, wherein the coating mixture powder has a particulate sulphidable copper compound content in a range of from 50% to 95% by weight.

13. A method according to claim 1, wherein the coating mixture consists of the particulate sulphidable copper compound and the particulate calcined, rehydratable alumina.

14. A method according to claim 1, wherein the surface layers of the coating mixture powder on the aged agglomerates have a thickness in a range of from 1 to 2000 micrometres.

15. A method according to claim 1, wherein the support material comprises a particulate calcined, rehydratable alumina, the coated agglomerates have a diameter in a range of from 1 mm to 15 mm and the surface layers of the coated agglomerates have a thickness in a range of from 1 μm to 2000 μm.

16. A method according to claim 1, wherein the coated agglomerates are aged for 0.5 to 8 hours before drying.

17. A method according to claim 1, wherein the coated agglomerates are dried at a temperature in a range of from 70 to 150° C.

18. A method for preparing a sorbent comprising preparing the dried sorbent precursor according to claim 1 and subjecting the dried sorbent precursor to a sulphiding step to convert the sulphidable copper compound to copper sulphide.

19. A method according to claim 18, wherein the sulphiding step is performed by reacting the copper compound with a sulphur compound that is hydrogen sulphide, alkali metal sulphide, ammonium sulphide, elemental sulphur or a polysulphide.

20. A method according to claim 18, wherein the sulphiding step is performed using hydrogen sulphide at a concentration in a range of from 0.1 to 5% by volume in an inert gas.

21. A method according to claim 18, wherein the sulphiding step is performed (i) ex-situ in a sulphiding vessel and a sulphiding agent is passed through the sulphiding vessel, or (ii) in situ in a vessel in which it is used to absorb heavy metals.

22. A dried sorbent precursor obtained by the method of claim 1.

23. A sorbent obtained by the method of claim 18.

24. A process for removing a heavy metal from a fluid stream comprising contacting the fluid stream with a sorbent of claim 23.

* * * * *